(12) United States Patent
DiSilvestro

(10) Patent No.: US 9,271,955 B2
(45) Date of Patent: Mar. 1, 2016

(54) NUTRITIONAL SUPPLEMENTS FOR EYE HEALTH AND RELATED METHODS

(71) Applicant: Ohio State Innovation Foundation, Columbus, OH (US)

(72) Inventor: Robert DiSilvestro, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/041,087

(22) Filed: Sep. 30, 2013

(65) Prior Publication Data

US 2014/0093489 A1     Apr. 3, 2014

Related U.S. Application Data

(60) Provisional application No. 61/707,235, filed on Sep. 28, 2012.

(51) Int. Cl.

| | |
|---|---|
| *A61K 31/355* | (2006.01) |
| *A61K 31/315* | (2006.01) |
| *A61K 31/30* | (2006.01) |
| *A61K 45/06* | (2006.01) |
| *A61K 31/122* | (2006.01) |
| *A61K 31/375* | (2006.01) |
| *A61K 33/30* | (2006.01) |
| *A61K 33/34* | (2006.01) |

(Continued)

(52) U.S. Cl.
CPC .............. *A61K 31/355* (2013.01); *A23L 1/302* (2013.01); *A23L 1/3045* (2013.01); *A61K 31/122* (2013.01); *A61K 31/30* (2013.01); *A61K 31/315* (2013.01); *A61K 31/375* (2013.01); *A61K 33/30* (2013.01); *A61K 33/34* (2013.01); *A61K 45/06* (2013.01); *A23V 2002/00* (2013.01)

(58) Field of Classification Search
CPC ..... A61K 31/07; A61K 31/30; A61K 31/315; A61K 31/355
See application file for complete search history.

(56) References Cited

U.S. PATENT DOCUMENTS

| | | | | |
|---|---|---|---|---|
| 4,200,337 | A * | 4/1980 | Jackovitz et al. | ................. 299/5 |
| 6,075,058 | A * | 6/2000 | Handelman | .......... A61K 31/047 514/729 |
| 6,291,533 | B1 * | 9/2001 | Fleischner | .................... 514/682 |

(Continued)

FOREIGN PATENT DOCUMENTS

| | | |
|---|---|---|
| WO | WO2005027950 A1 | 3/2005 |
| WO | WO2009031788 A1 | 3/2009 |

OTHER PUBLICATIONS

International Search Report and Written Opinion for International Application No. PCT/US2013/062383 filed Sep. 27, 2013 corresponding to U.S. Appl. No. 14/041,087.

(Continued)

*Primary Examiner* — Rosanne Kosson
(74) *Attorney, Agent, or Firm* — Roger D. Emerson; Emerson Thomson Bennett, LLC

(57) ABSTRACT

A nutritional or dietary supplement composition that strengthens and promotes a general eye health benefit for aging adults, including retinal health through the prevention, stabilization, reversal and/or treatment of visual acuity loss by reducing the risk of developing late stage or advanced age-related macular degeneration in persons with early age-related macular degeneration. The nutritional or dietary supplement composition may likewise reduce the risk of vision loss associated with the development of cataracts.

16 Claims, 5 Drawing Sheets

Coenzyme Q Effects on Serum Vitamin C

(51) Int. Cl.
A23L 1/302 (2006.01)
A23L 1/304 (2006.01)

(56) References Cited

U.S. PATENT DOCUMENTS

| | | | |
|---|---|---|---|
| 6,649,195 | B1 | 11/2003 | Gorsek |
| 6,660,297 | B2 | 12/2003 | Bartels et al. |
| 7,267,830 | B2 | 9/2007 | Lang |
| 7,842,722 | B2 | 11/2010 | Lang |
| 2003/0003162 | A1 | 1/2003 | Rath |
| 2008/0038368 | A1* | 2/2008 | Geibel et al. ............... 424/641 |

OTHER PUBLICATIONS

Pavlovic, et al. "The Effect of Coenzyme Q10 on Blood Ascorbic Acid, Vitamin E, and Lipid Peroxide in Chronic Cadmium Intoxication", Journal of Environmental Pathology, Toxicology and Oncology, 20(2)122-140 (2001).

Singh, et al. "Effect of hydrosoluble coenzyme Q10 on blood pressures and insulin resistance in hypertensive patients with coronary artery disease", Journal of Human Hypertension (1999) 13, 203-208, 1999 Stockton Press.

https://web.archive.org/web/20120721131915/http:/www.mindbodyhealth.com/MbhVision20.htm; Archived web page for "http://www.mindbodyhealth.com/MbhVision20.htm"; Archived Jul. 21, 2012.

Linus Pauling Institute at Oregon State University, "Carotenoids—Alpha-Carotene, Beta-Carotene, Beta-Cryptoxanthin, Lycopene, Lutein, and Zeaxanthin"; "http://lpi.oregonstate.edu/infocenter/pytochemicals/carotenoids/"; Accessed Mar. 23, 2015.

ConsumerLab.com, "Product Review: Zinc Supplements and Lozenges—Which Zinc Products are Best for Treating a Cold or Reversing Zinc Deficiency?"; "https://www.consumerlab.com/reviews/Zinc-Supplements-Lozenges-Review/zinc"; Accessed Mar. 23, 2015.

National Institutes of Health Office of Dietary Supplements, "Zinc Fact Sheet for Health Professionals"; "http://ods.od.nih.gov/factsheets/Zinc-HealthProfessional/"; Accessed Mar. 23, 2015.

National Institutes of Health Office of Dietary Supplements, "Copper—Determinants of Copper Needs Across the Life Span"; "http://ods.od.nih.gov/News/Copper.aspx"; Accessed Mar. 23, 2015.

Harrington, M., et al., "A comparison of the bioavailability of ferrous fumarate and ferrous sulfate in nonn-anemic Mexican women and children consuming a sweetened maize and milk drink"; European Journal of Clinical Nutrition (2011) 65, 20-25; doi:10.1038/ejcn.2010.18; published online Sep. 15, 2010.

DiSilvestro, R., "Enhanced aerobic exercise performance in women by a combination of three mineral chelates plus two conditionally essential nutrients (634.7)"; The Journal of the Federation of American Societies for Experimental Biology, vol. 28, No. 1, Supplement 634.7, Apr. 2014.

* cited by examiner

NUTRITIONAL SUPPLEMENTS FOR EYE HEALTH AND RELATED METHODS

FIELD OF INVENTION

The present invention relates to a nutritional or dietary supplement composition that strengthens and promotes a general eye health benefit for aging adults, including retinal health through the prevention, stabilization, reversal and/or treatment of visual acuity loss in people with particular ocular diseases. More specifically, the present invention relates to particularly effective combination of specific minerals, vitamins, and non-essential nutritional agents that decrease visual acuity loss by reducing the risk of developing late stage or advanced age-related macular degeneration in persons with early age-related macular degeneration. The subject composition may likewise reduce the risk of vision loss associated with the development of cataracts.

BACKGROUND

Macular degeneration associated with age is the leading cause of severe visual acuity loss in the United States and Western Europe in persons aged 55 years old or older. The cause of macular degeneration is unknown.

Many nutritional supplements are currently on the market for vision support, including those under the following brand names: Xanthalin, Xantha View, Vision Essentials, Occulo Nutrients, Vision Defense 14, Eye Shield, Eye Rite, Macular Degeneration, and Occuplex w/Lutein (among others). U.S. Pat. Nos. 7,842,722, 7,267,830, 6,649,195, 660,297 provide a few examples.

Previously-available supplements comprise different formulations from the present invention. Moreover, the present formulation provides surprising results compared to the other vision-related nutritional supplements.

SUMMARY OF THE INVENTION

Figure 1:
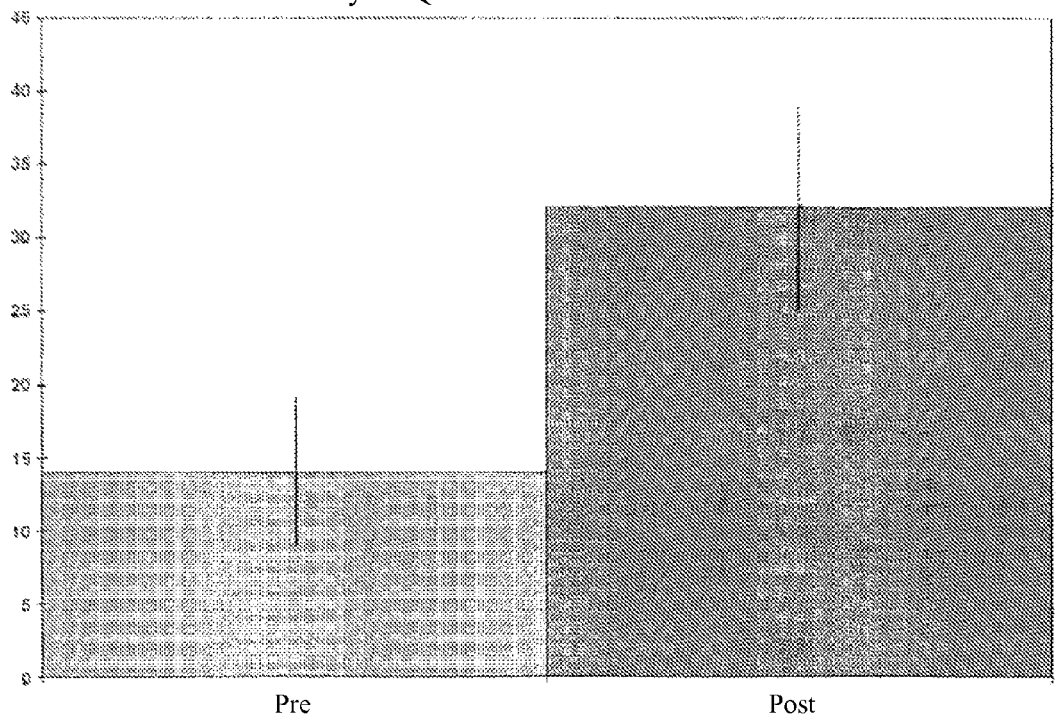
FIG. 1. Coenzyme Q supplementation effect on serum vitamin C (µg/ml). Subjects (N=12) were given coenzyme Q for 2 weeks with blood taken pre and post intervention. Values are means±SD. Post-values were significantly different from pre-values by paired t-test (P<0.001).

The present invention is a nutritional or dietary supplement composition for administration to humans or other animals that strengthens and promotes general eye health and retinal health through the prevention, stabilization, reversal and/or treatment of visual acuity loss in people with particular ocular diseases. The present nutritional or dietary supplement composition may also be administered to prevent, stabilize, reverse and/or treat cataract development. The present nutritional or dietary supplement composition is shown herein to reduce visual acuity loss. Visual acuity loss is decreased through the use of the present composition by reducing the risk of developing late stage or advanced age-related macular degeneration in persons with early age-related macular degeneration. The present composition may likewise reduce the risk of visual acuity loss associated with the development of cataracts. The present composition may also prevent or reduce symptoms of dry eye.

The unique formulation of essential ingredients of the nutritional or dietary supplement composition of the present invention is demonstrated herein to provide surprising benefits for safe and effective prevention, stabilization, reversal and/or treatment of macular degeneration or visual acuity loss. The essential ingredients of the subject nutritional or dietary supplement composition, considered individually, have been known to provide certain physiological effects. However, the subject unique formulation and the effects thereof on eye health were not previously known.

The present invention likewise provides a method of treating a human or other animal by administering a nutritional or dietary supplement composition comprising an effective amount of specific nutrients to decrease visual acuity loss. The practice of this invention involves supplementing the diet of humans or animals by oral, intraperitoneal, intravenous, subcutaneous, transcutaneous or intramuscular routes of administration.

The present invention likewise provides a method of manufacturing a nutritional or dietary supplement composition comprising an effective amount of specific nutrients to decrease visual acuity loss.

Accordingly, it is an object of the present invention to provide a nutritional or dietary supplement composition effective in the prevention, stabilization, reversal and/or treatment of macular degeneration and/or visual acuity loss.

Another object of the present invention is to provide a safe nutritional or dietary supplement composition for the prevention, stabilization, reversal and/or treatment of macular degeneration and/or visual acuity loss.

Another object of the present invention is to provide an effective method of preventing, stabilizing, reversing and/or treating macular degeneration and/or visual acuity loss.

Another object of the present invention is to provide a safe method of preventing, stabilizing, reversing and/or treating macular degeneration and/or visual acuity loss.

Another object of the present invention is to provide a method of manufacturing a safe nutritional or dietary supplement composition for the prevention, stabilization, reversal and/or treatment of macular degeneration and/or visual acuity loss.

Still another object of the present invention is to provide a method of manufacturing a nutritional or dietary supplement composition effective in the prevention, stabilization, reversal and/or treatment of macular degeneration and/or visual acuity loss.

The present invention therefore provides nutrition supplement compositions comprising on a daily dosage basis: approximately 0.5-5 mg copper, as copper glycinate, approximately 12-50 to mg zinc, as zinc glycinate, and approximately 100-500 IU natural vitamin E.

In one embodiment, the present invention provides nutrition supplement compositions which comprise approximately 1-5 mg copper, as copper glycinate, approximately 15-50 mg zinc, as zinc glycinate, and approximately 200-500 IU natural vitamin E.

In one embodiment, the present invention provides nutrition supplement compositions which comprise approximately 1-3 mg copper, as copper glycinate, and 20-40 mg zinc, as zinc glycinate, and 350-450 IU natural vitamin E.

In one embodiment, the present invention provides nutrition supplement compositions which comprise approximately 2 mg copper, as copper glycinate, and approximately 30 mg zinc, as zinc glycinate, and approximately 400 IU natural vitamin E.

The present invention therefore provides nutrition supplement compositions comprising on a daily dosage basis: approximately 0.25 to 2.5 times the Daily Value of copper, as copper glycinate, and approximately 0.8 to 3.3 times the Daily Value of zinc, as zinc glycinate, and approximately 3.3 to 16.6 times the Daily Value of natural vitamin E.

In one embodiment, the present invention provides nutrition supplement compositions comprising on a daily dosage basis: approximately 0.5 to 2.5 times the Daily Value of copper, as copper glycinate, and approximately 1 to 3.3 times the Daily Value of zinc, as zinc glycinate, and approximately 6.6 to 16.6 times the Daily Value of natural vitamin E.

In one embodiment, the present invention provides nutrition supplement compositions comprising on a daily dosage basis: approximately 0.5 to 1.5 times the Daily Value of copper, as copper glycinate, and approximately 1.3 to 2.6 times the Daily Value of zinc, as zinc glycinate, and approximately 11.6 to 15 times the Daily Value of natural vitamin E.

In one embodiment, the present invention provides nutrition supplement compositions comprising on a daily dosage basis: approximately 1 times the Daily Value of copper, as copper glycinate, and approximately 2 times the Daily Value of zinc, as zinc glycinate, and approximately 13.3 times the Daily Value of natural vitamin E.

Moreover, the present invention provides nutrition supplement compositions as described, which further comprise one or more of a nutrient selected from the group consisting of: vitamin C, coenzyme Q, manganese as manganese glycinate, lutein, and zeaxanthin.

Moreover, the present invention provides nutrition supplement compositions as described, which further comprise one or more of a nutrient selected from the group consisting of: lutein-zeaxanthin, quercetin, phenolic compounds, lipoic acid, and taurine.

Moreover, the present invention provides nutrition supplement compositions as described, formulated as an oral nutrition delivery vehicle selected from the group consisting of: tablet, capsule, food, and drink.

Moreover, the present invention provides nutrition supplement compositions as described, formulated for a mammal selected from the group consisting of horse, dog, cat, cattle and human.

Moreover, the present invention provides methods of manufacturing a composition as described comprising: blending any composition herein into a vehicle for oral nutrition delivery.

In one embodiment, the methods herein include those wherein said vehicle for oral nutrition delivery is selected from the group consisting of: tablet, capsule, food, and drink.

Also provided are methods of supporting eye health, comprising administering a composition herein.

Also provided are methods of ameliorating vision loss, comprising administering a composition of any of the claims herein.

Also provided are methods of ameliorating macular degeneration-associated symptoms, comprising administering a composition of any of the claims herein.

Also provided are methods of treating macular degeneration, comprising administering a composition of any of the claims herein.

Also provided are methods of increasing plasma concentrations of vitamin C in a mammal, comprising administering coenzyme Q to the mammal. In one such embodiment, vitamin C is co-administered.

Also provided are methods of increasing retention and stability of vitamin C in a mammal, comprising administering coenzyme Q to the mammal. In one such embodiment, vitamin C is co-administered.

Also provided are methods of increasing plasma concentrations of vitamin E in a mammal, comprising administering coenzyme Q to the mammal. In one such embodiment, vitamin E is co-administered.

Also provided are methods of increasing retention and stability of vitamin E in a mammal, comprising administering coenzyme Q to the mammal. In one such embodiment, vitamin E is co-administered.

These and other objectives and advantages of the present invention, some of which are specifically described and others that are not, will become apparent from the detailed description and claims that follow.

DETAILED DESCRIPTION

The following detailed description is provided to enable any person skilled in the art to which the present invention pertains to make and use the same, and sets forth the best mode contemplated by the inventors of carrying out the subject invention.

Compositions

Three specific nutrients (copper, as copper glycinate, zinc, as zinc glycinate, and natural vitamin E) in combination have been shown to be superior than prior formulations in supporting healthy vision.

Tables 1 describe ranges for each nutrient in weight or IU, along with ranges of certain optional nutrients. Each range of the composition nutrients is independent from the ranges of the other indicated nutrients. For instance, in devising a formulation from Table 1, copper as copper glycinate may be selected from the range indicated in Range 1 (eg. 0.6 mg), zinc as zinc glycinate may be selected from the range indicated in Range 3 (eg. 39 mg), natural vitamin E may be selected from the range indicated in Range 2 (eg. 250 IU) and lutein may be selected from the range indicated in Range 4 (eg. approx. 12 mg).

Table 2 is a convenient translation of Table 1 into United States Recommended Daily Allowance (USRDA) by percentage of defined diet, when an USRDA has been determined by the United States.

TABLE 1

Daily Dosage, by weight

| Nutrient | Range 1 | Range 2 | Range 3 | Range 4 |
|---|---|---|---|---|
| Copper, as copper glycinate | 0.5-5 mg | 1-5 mg | 1-3 mg | Approx. 2 mg |
| Zinc, as zinc glycinate | 12-50 mg | 15-50 mg | 20-40 mg | Approx. 30 mg |
| Natural vitamin E (d-alpha-tocopherol) | 100-500 IU | 200-500 IU | 350-450 IU | Approx. 400 IU |
| Vitamin C | 0-1000 mg | 100-600 mg | 450-550 mg | Approx. 500 mg |
| Coenzyme Q | 0-100 mg | 25-75 mg | 40-60 mg | Approx. 50 mg |
| Manganese, as manganese gycinate | 0-10 mg | 2-8 mg | 4-6 mg | Approx. 5 mg |
| Lutein | 0-20 mg | 5-15 mg | 9-12 mg | Approx. 10 mg |
| Zeaxanthin | 0-5 mg | 1-5 mg | 1-3 mg | Approx. 2 mg |

TABLE 2

Daily Dosage, by Daily Value Multiplier

| Nutrient | Daily Value | Daily Value Multiplier 1 | Daily Value Multiplier 2 | Daily Value Multiplier 3 | Daily Value Multiplier 4 |
|---|---|---|---|---|---|
| Copper, as copper glycinate | 2 mg | .25 to 2.5 | .5 to 2.5 | .5 to 1.5 | Approx 1 |
| Zinc, as zinc glycinate | 15 mg | .8 to 3.3 | 1 to 3.3 | 1.3 to 2.6 | Approx 2 |
| Natural vitamin E | 30 IU | 3.3 to 16.6 | 6.6 to 16.6 | 11.6 to 15 | Approx 13.3 |
| Vitamin C | 60 mg | 0 to 16.6 | 1.6 to 10 | 7.5 to 9.2 | Approx 8.3 |
| Coenzyme Q | No Daily Value | | | | |
| Manganese, as manganese glycinate | 2 mg | 0 to 5 | 1 to 4 | 2 to 3 | Approx 2.5 |
| Lutein | No Daily Value | | | | |
| Zeaxanthin | No Daily Value | | | | |

Copper, as Copper Glycinate

Figure 4:
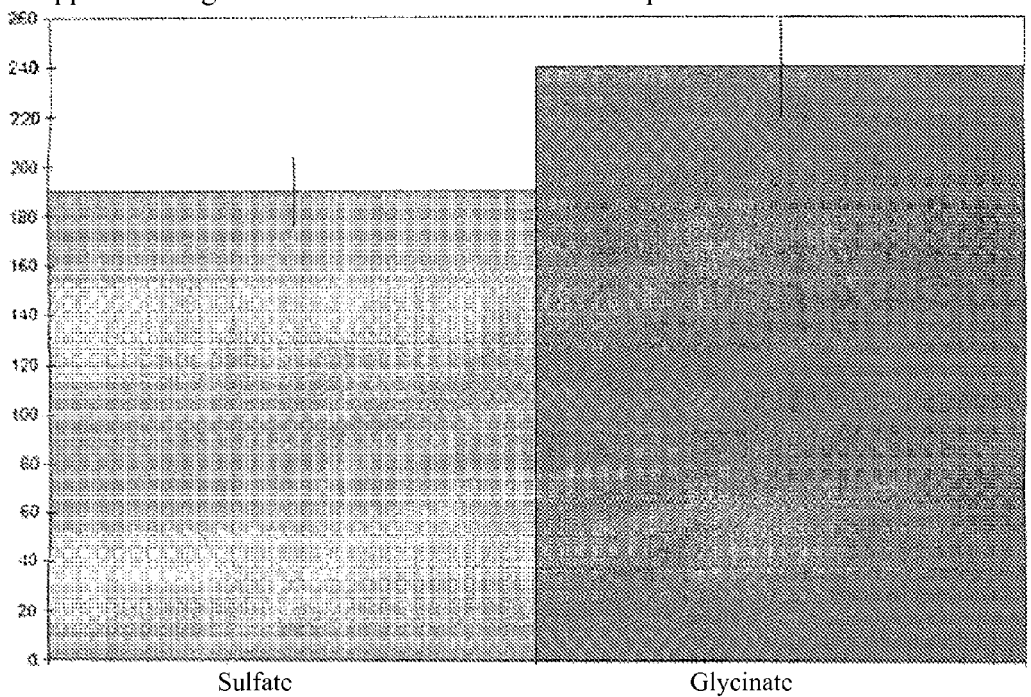
FIG. 4. Comparison of adequate copper intake as sulfate or glycinate for effects on plasma extracellular superoxide dismutase activities in rats. Rats were fed the copper for 6 weeks. Glycinate values were significantly different from sulfate values by unpaired t-test (P<0.01). Values are means±SD in activity units/ml.

Copper is another important cofactor for metalloenzymes, and is a second necessary cofactor for superoxide dismutase. The inventor discovered that, when copper was fed at supposedly adequate levels, copper glycinate gave higher activities of a plasma copper enzyme than copper sulfate (FIG. 4).

Daily Dose, by Weight.

Accordingly, preferably each daily dosage contains approximately 0.5 to 5 mg of copper as copper glycinate. Such a formulation provides a total daily dosage of 1 to 5 mg, but more preferably approximately 1 to 3 mg, of copper as copper glycinate and preferably approximately 2 mg copper as copper glycinate. This weight percentage for copper as copper glycinate may represent approximately a twenty-five to sixty percent overage per tablet of additional copper as copper glycinate in the delivery vehicle formulation to ensure product potency over the shelf life of the delivery vehicle.

Daily Dose, by Daily Value Multiplier.

Two mg is the Daily Value for copper. Accordingly, copper as copper glycinate represents approximately 0.25 to 2.5 times the Daily Value for copper, preferably approximately 0.5 to 2.5 times the Daily Value, more preferably approximately 0.5 to 1.5 times the Daily Value, but most preferably approximately 1 times the Daily Value.

Zinc, as Zinc Glycinate

Figure 2:
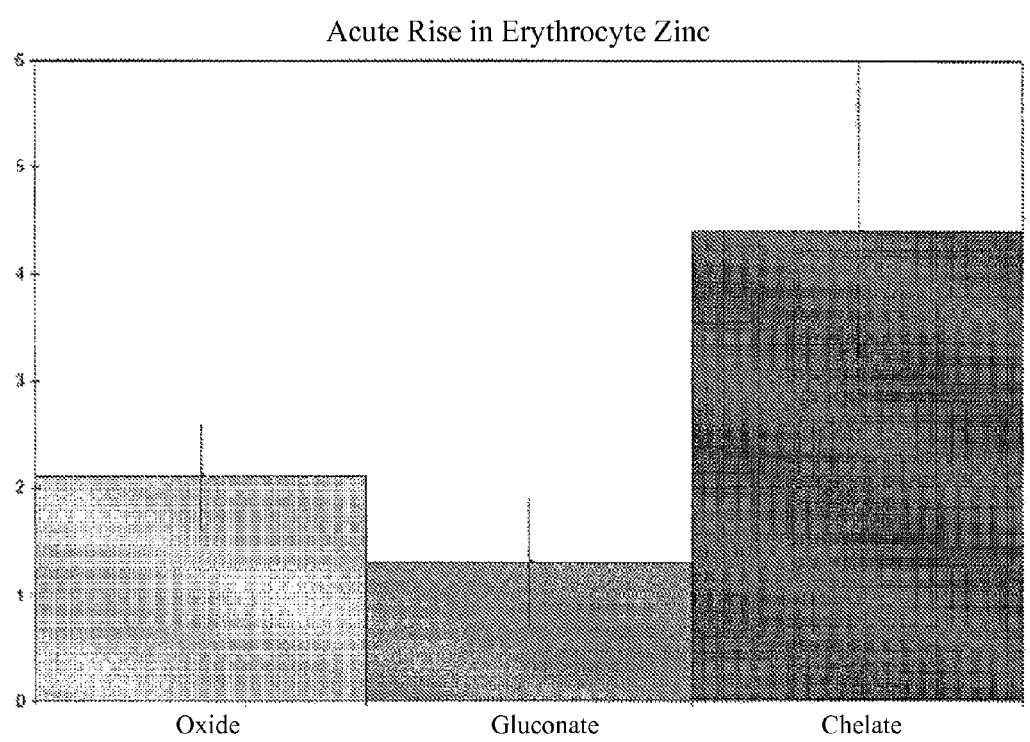
FIG. 2. Relative zinc absorption from three different forms of zinc. Subjects (n=12) were given one dose of zinc with blood samples taken at 0, 1, 2, 3, and 4 hours. Erythrocyte (red blood cell) zinc was analyzed for each time point with area under the curve used as a measure of relative absorption. The order of the different forms of zinc was randomly determined for each subject. A washout of at least 2 weeks occurred between testings of the different forms of zinc. Values are means±SD. Zinc chelate values differed from the other two groups by ANOVA+Tukey multiple comparison test (p<0.05)
Figure 3:
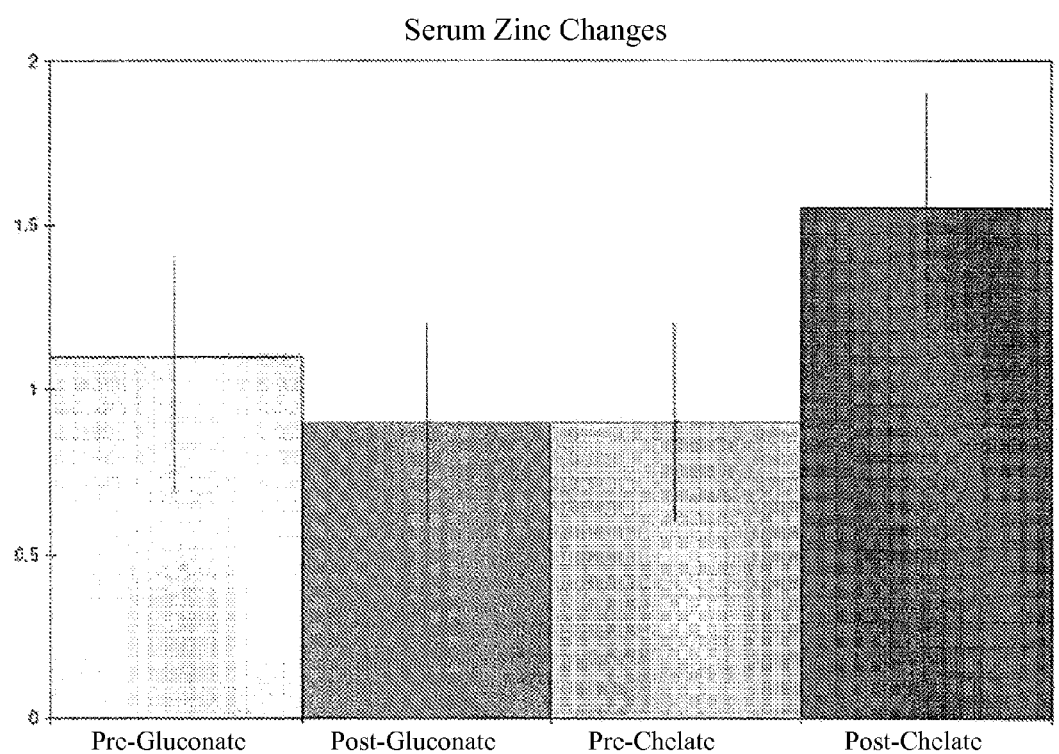
FIG. 3. Plasma zinc (µg/ml) response to zinc supplementation as gluconate (GLUC) or glycinate chelate (CHE). Young adult females were given 60 mg/day zinc for 6 weeks. Post treatment values for the glycinate were significantly different from pre-treatment (p<0.001, paired t-test). The gluconate group actually showed a statistically significant decrease (p<0.05)

Zinc is important in maintaining the health of an eye's retina and is an essential part of more than 100 enzymes involved in digestion, metabolism, reproduction, and wound healing. The present inventor discovered that, in young adult women, zinc glycinate is better absorbed than zinc oxide (FIG. 2). Moreover, it has now been discovered that zinc glycinate has superior attributes of compared to zinc gluconate. (FIG. 3).

Daily Dose, by Weight.

Preferably, the subject composition provides a total daily dosage of preferably 12 to 50 mg, of zinc, as zinc glycinate, more preferably 15 to 50 mg, more preferably 20 to 40 mg and more preferably approximately 30 mg of zinc, as zinc glycinate. This weight percentage for copper as zinc glycinate may represent approximately a twenty-five to sixty percent overage per tablet of additional copper as zinc glycinate in the delivery vehicle formulation to ensure product potency over the shelf life of the delivery vehicle.

Daily Dose, by Daily Value Multiplier.

The Daily Value for zinc is approximately 15 mg. The present daily dosage of zinc is equivalent to approximately 0.8 to 3.3 times the Daily Value for zinc, preferably approximately 1 to 3.3 times the Daily Value, more preferably approximately 1.3 to 2.6 times the Daily Value, most preferably approximately 2 times the Daily Value of zinc as zinc glycinate.

Natural Vitamin E

Vitamin E is an antioxidant.

Daily Dose, by International Units (IU).

Preferably each daily dosage of the subject composition provides 100 to 500 IU of natural vitamin E in the form of d-alpha tocopherol succinate, more preferably approximately 200 to 500 IU, more preferably approximately 350 to 540 IU, more preferably approximately 400 IU. This weight percentage for vitamin E may represent approximately a twenty-five to sixty percent overage per tablet of additional vitamin E in the delivery vehicle formulation to ensure product potency over the shelf life of the delivery vehicle.

Daily Dose, by Daily Value Multiplier.

The Daily Value of vitamin E in the form of dl-alpha tocopheryl acetate is 30 IU. The present invention comprises d-alpha tocopherol succinate (natural vitamin E). This daily dosage of vitamin E is equivalent to approximately 3.3 to 16.6 times the Daily Value for vitamin E, preferably approximately 6.6 to 16.6 time the Daily Value, more preferably approximately 11.6 to 15 times the Daily Value, most preferably approximately 13.3 times the Daily Value for vitamin E.

Optional Ingredients

Other ingredients may likewise be added to the nutritional or dietary composition of the present invention if desired. Such ingredients include for example but are not limited to vitamin C, coenzyme Q, lutein, zeaxanthin, lipoic acid, and phenolic compounds such as for example but not limited to oligomeric proanthocyanidins, and combinations thereof as is discussed in more detail below.

Vitamin C

Vitamin C is a water-soluble antioxidant.

Daily Dose, by Weight.

Each daily dosage of the subject composition optionally delivers approximately 0 to 1000 mg of vitamin C, but more preferably approximately 100 to 600 mg vitamin C, more preferably 450 to 550 mg, more preferably approximately 500 mg. The most preferred form of vitamin C is ascorbic acid. This weight percentage for vitamin C may represent up to an approximately twenty percent overage to compensate for natural degradation of ascorbic acid over the shelf life of the delivery vehicle.

Daily Dose, by Daily Value Multiplier.

The U.S. recommended dietary allowance (Daily Value) for vitamin C in the form of ascorbic acid is 60 mg. Very large daily doses of vitamin C have been taken over many years with no or only minor undesirable effects. This daily dosage of vitamin C is equivalent to approximately 0 to 16.6 times the Daily Value, preferably approximately 1.6 to 10 times the Daily Value, more preferably approximately 7.5 to 9.2 times the Daily Value, most preferably approximately 8.3 times the Daily Value of vitamin C.

Ascorbic acid is the preferred source of vitamin C in the subject tablets, although other sources such as for example sodium ascorbate could alternatively be used.

Coenzyme Q

Coenzyme Q has antioxidant properties. This molecule is found in the diet and is made by the body. Body production declines with age. Absorption of orally ingested coenzyme Q can be low, though certain forms work better than others. As shown in FIG. 1, herein, a well-absorbed form of this semi-essential nutrient surprisingly can greatly increase plasma concentrations of active vitamin C.

Daily Dose, by Weight.

Each daily dosage of the subject composition optionally delivers approximately 0 to 100 mg of coenzyme Q, but more preferably approximately 25 to 75 mg coenzyme Q, more preferably approximately 40 to 60 mg, more preferably approximately 50 mg. This weight percentage coenzyme Q may include an approximately twenty-five to sixty percent overage of coenzyme Q in the delivery vehicle formulation to ensure product potency over the shelf life of the delivery vehicle.

Manganese, as Manganese Glycinate

Manganese is needed for function of the antioxidant enzyme known as Mn superoxide dismutase (4), which is also called superoxide dismutase 2 or SOD2. Macular degeneration-like symptoms form in mice genetically manipulated to have low activities of SOD2 (17, 18). FIG. 4 shows that MN SOD2 interacts with lutein/zeathin, and manganese. Lutein/zeaxanthin can increase eye zeaxanthin. This increase might not occur in the presence of moderate manganese deficiency. Since moderate manganese deficiencies occur commonly in people, the inventive product gives a solution for correcting the eye-specific deficiency.

Figure 5:
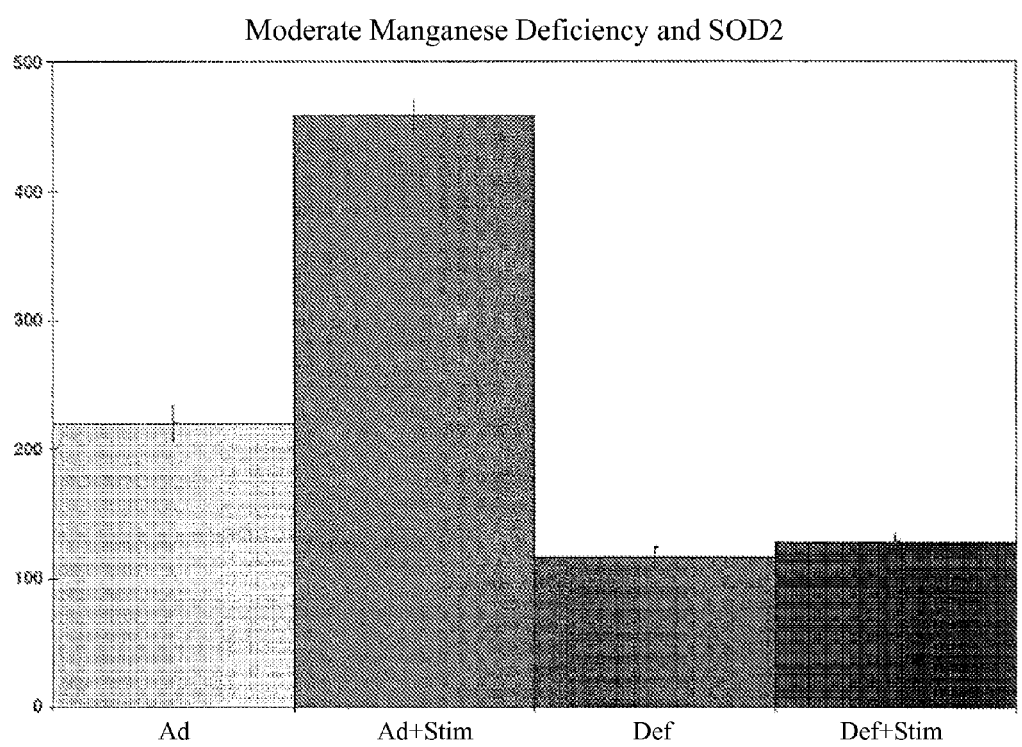
FIG. 5. Lung SOD2 activities (Units/g tissue+SD) in manganese adequate and marginally deficient rats. Rats were fed diets for 6 weeks to produce adequate manganese status (Ad) or moderately deficient manganese status (Def). Some rats were given an unnamed agent to stimulate an increase in SOD2 activities (+Stim).

FIG. 5 shows that moderate manganese deficiency in rats prevents increases in tissue SOD2 activity due to treatment with a certain agent. This surprisingly shows that stimulation of MnSOD2 activity can be limited by a moderate deficiency of manganese.

Daily Dose, by Weight.

Each daily dosage of the subject composition optionally delivers approximately 0 to 10 mg of manganese, as manganese glycinate, but more preferably approximately 2 to 8 mg manganese, more preferably approximately 4 to 6 mg, more preferably approximately 50 mg. This weight percentage manganese as manganese glycinate may include approximately a twenty-five to sixty percent overage of manganese in the delivery vehicle formulation to ensure product potency over the shelf life of the delivery vehicle.

Two mg is the Daily Value for manganese. Accordingly, manganese as manganese glycinate represents approximately 0 to 5 times the Daily Value for manganese, preferably approximately 1 to 4 times the Daily Value, more preferably approximately 2 to 3 times the Daily Value, most preferably approximately 2.5 times the Daily Value for manganese as manganese glycinate.

Lutein

Lutein is one of the most abundant carotenoids found in fruits and vegetables. Lutein is also an antioxidant found in the retina of healthy eyes.

Preferably each daily dosage could provide approximately 0 to 20 mg of lutein, more preferably 5 to 17 mg, more preferably 9 to 15 mg, more preferably approximately 12 mg. The lutein may be a conventional lutein or a high-absorption lutein, such as, but not limited to, solid, lipidated, phospholipidated, micellular, or lecithinized lutein.

Zeaxanthin

Zeaxanthin is a carotenoid. Zeaxanthin is found naturally in fruits and vegetables. Zeaxanthin is also an antioxidant found in the retina of healthy eyes.

Preferably each daily dosage could provide 0 to 5 mg of zeaxanthin, more preferably 1 to 5 mg, more preferably 1 to 3 mg, more preferably approximately 2 mg.

Lutein-Zeaxanthin

Lutein-zeaxanthin raw material combinations achieved deliberately, because of normal composition, or through raw material contamination may likewise be added to the subject composition as desired. Preferred ratios of lutein-zeaxanthin for example include 90 to 99 percent lutein and 1 to 10 percent zeaxanthin or 90 to 99 percent zeaxanthin and 1 to 10 percent lutein. Preferably the daily dosage could provide approximately 0.01 to 10 mg of lutein-zeaxanthin for a total daily dosage of approximately 0.04 to 40 mg.

Phenolic Compounds

Phenolic compounds such as oligomeric proanthocyanidins are additional useful antioxidants. Oligomeric proanthocyanidins are found naturally in grape seeds. Phenolic compounds may be added to the nutritional or dietary supplement composition of the present invention if desired. If so desired, preferably each daily dosage would provide approximately 0.25 to 5 mg of phenolic compounds for a total daily dosage of approximately 1 to 20 mg.

Lipoic Acid

Lipoic acid provides superior antioxidant protection due to the fact that it enhances the potency of other antioxidants in the body. Lipoic acid may be added to the nutritional or dietary supplement composition of the present invention if desired.

If so desired, preferably each daily dosage would provide approximately 0 to 150 mg lipoic acid, more preferably 50 to 130 mg, more preferably approximately 75 to 125 mg, more preferably approximately 100 mg.

Taurine

Taurine is a known antioxidant.

If so desired, preferably each daily dosage would provide approximately 0 to 150 mg taurine, more preferably approximately 50 to 130 mg, more preferably approximately 75 to 125 mg, more preferably approximately 100 mg.

Quercetin

If so desired, preferably each daily dosage would provide approximately 0 to 100 mg quercetin, more preferably approximately 20 to 80 mg, more preferably approximately 50 to 70 mg, most preferably approximately 60 mg.

Methods of Manufacturing, Formulating and Delivering

A method of manufacturing the nutritional or dietary supplement composition of the present invention, which is safe and effective in the prevention, stabilization, reversal and/or treatment of macular degeneration or visual acuity loss by reducing the risk of developing late stage or advanced age-related macular degeneration in persons with early age-related macular degeneration and/or by reducing the risk of vision loss associated with the development of cataracts, includes providing the essential ingredients in accordance with the formulation noted above. The essential ingredients of the subject composition, as well as any desired inactive ingredients and/or additive ingredients are combined by weight as described above and mechanically combined, such as for example, through the use of a blender to form a blend. If necessary, the blend is then tumbled until uniform. The blend is then compressed using a tablet press to form tablets. Optionally a coating may be sprayed on the tablets and the tablets tumbled until dry. Alternatively, the blend may be placed in mineral oil to form a slurry for containment in a soft gel capsule, the blend may be placed in a gelatin capsule or the blend may be placed in other dosage forms known to those skilled in the art.

The subject composition is formulated to provide the above-listed essential ingredients at preferably not less than the daily dosage amounts specified above. This particular formulation of the subject composition has unexpectedly been shown to provide a greater protective effect on the health of eyes than that achieved through the administration of a placebo, the antioxidant ingredients or the zinc/copper ingredients independently. The subject composition is preferably provided for oral administration in the form of lacquered tablets, unlacquered tablets, caplets or capsules. For purposes of simplicity only, throughout the remainder of this detailed description lacquered tablets, unlacquered tablets, caplets and capsules will each be referred to as simply "tablets" without distinction in form or function.

The preferred daily dosage of the subject composition as specified above may be administered in the form of two or more tablets. Most preferably the daily dosage of the subject composition is provided in the form of one tablet taken twice daily, for a total of two tablets a day, or in the form of two tablets taken twice daily, for a total of four tablets a day. Compared to taking the total daily dose once a day, twice daily dosing of half the total daily dose in one or more tablets per dose provides improved absorption and better maintenance of blood levels of the essential ingredients.

Tablets of the preferred formulation of the subject composition contain larger quantities of essential ingredients per tablet than the minimum quantities per tablet specified above. The minimum quantities specified above, per tablet, reflect the minimum amount of each essential ingredient to be provided upon oral administration through to the date of tablet expiration as set forth on the tablet sale label. However, since essential ingredients are subject to degradation over time, the tablets must contain larger quantities of essential ingredients to compensate for ingredient degradation. By providing larger quantities of essential ingredients in each tablet, one is ensured that even with ingredient degradation, one hundred percent of the ingredient amount specified on the tablet sale label is provided upon oral administration of the tablet through to the specified expiration date of the tablet. Another consideration in formulating the subject composition is that depending on the source of the individual ingredients, individual ingredient degradation rates may vary.

Accordingly, the specific formulation of the subject composition will vary depending on the sources of the individual ingredients and the specified length of product shelf life before expiration. Typically, the product shelf life for nutritional or dietary supplements is approximately two to three years. Such ingredient overages to compensate for ingredient degradation is reflected in the preferred ingredient percentage weight per tablet information provided below. Tablet formulations may also vary somewhat depending on slight deviations from manufacturing specifications within controlled tolerance ranges as customary within the field of art.

Variations contemplated in administering the subject composition to humans or other animals include, but are not limited to, providing time-release tablets or tablets manufactured to be administered as a single dose or as other multiple part dosages. Additionally, alternative avenues of administration besides oral administration are contemplated herein such as for example, but not limited to, intraperitoneal, intravenous, subcutaneous, sublingual, transcutaneous, intramuscular or like forms of administration. Each tablet of the subject composition preferably contains the following essential ingredients in the quantities specified below including overages to compensate for ingredient degradation.

For instance, the composition may appear, for example, in the form of all kinds of food, feed, drink, functional food and functional feed, e.g. as bread, cookies and biscuits, cheese and other dairy products, chocolate, jam, pudding and other dairy desserts, spreadable products, frozen desserts and ice-cream; in the form of a pharmaceutical composition and medicament, e.g. as a powder, an aggregate, a granulate, a tablet, a coated tablet, a lozenge, a capsule, a drink, a syrup, a composition for tube feeding, for enteral intake, for oral administration and for enteral administration.

The composition may be useful as a supplement for any animal susceptible to vision problems, including, for example, horses, dogs, cats, cattle, and humans.

While there is described herein certain specific embodiments of the present invention, it will be manifest to those skilled in the art that various modifications may be made without departing from the spirit and scope of the underlying inventive concept and that the same is not limited to the particular forms herein described except insofar as indicated by the scope of the appended claims.

EXAMPLES

Example 1

Preliminary Experiments, as Summarized in the Figures

Example 2

Comparison Studies

These studies will compare the present formula to the PreserVision AREDS2 formula. The study will not actually assess the progress of macular degeneration, which can take 5 to 10 years to do. Instead, the study will evaluate functional capacities of the nutritional agents given, and look at processes relevant to aging eye health, including macular degeneration. The latter will include eye glare recovery, analysis of tear components, blood levels of auto-antibodies indicative of eye tissue wear and injury, and blood indicators of inflammation which correlate with risk of macular degeneration.

Example 3

Formulation 1 (tablets)
Formulation 2 (drink)
Formulation 3 (food)
Formulation 4 (other)
Control Formulation(s)

What is claimed is:

1. A nutrition supplement composition for an eye comprising on a daily dosage basis: approximately 0.5-5 mg copper, as copper glycinate, approximately 12-50 mg zinc, as zinc glycinate, approximately 100-500 IU natural vitamin E and high-absorption phospholipidated lutein.

2. The nutrition supplement of claim 1, which comprises approximately 1-5 mg copper, as copper glycinate, approximately 15-50 mg zinc, as zinc glycinate, and approximately 200-500 IU natural vitamin E.

3. The nutrition supplement of claim 2, which comprises approximately 1-3 mg copper, as copper glycinate, approximately 20-40 mg zinc, as zinc glycinate, and approximately 350-450 IU natural vitamin E.

4. The nutrition supplement of claim 3, which comprises approximately 2 mg copper, as copper glycinate, approximately 30 mg zinc, as zinc glycinate, and approximately 400 IU natural vitamin E.

5. The composition of claim 1, which further comprises one or more of a nutrient selected from the group consisting of: vitamin C, coenzyme Q, manganese as manganese glycinate, zeaxanthin, lutein-zeaxanthin combination, quercetin, phenolic compounds, lipoic acid, and taurine.

6. The composition of claim 1, further comprising an oral nutrition delivery vehicle selected from the group consisting of: tablet, capsule, food, and drink.

7. A method of manufacturing a composition comprising: blending a composition of claim 1 into a vehicle for oral nutrition delivery.

8. The method of claim 7 wherein said vehicle for oral nutrition delivery is selected from the group consisting of: tablet, capsule, food, and drink.

9. A method of supporting eye health, comprising administering the composition of claim 1, to a human.

10. A method of ameliorating vision loss, comprising administering the composition of claim 1 to a subject in need thereof.

11. A method of treating macular degeneration, comprising administering the composition of claim 1 to a subject in need thereof.

12. The method of claim 9, wherein the composition further comprises coenzyme Q to increase plasma concentrations of vitamin C in the human.

13. The method of claim 12, wherein vitamin C is co-administered.

14. The method of claim 12, further comprising verifying the increased retention and stability of vitamin C in the human.

15. The method of claim 12, wherein vitamin E is co-administered.

16. A nutrition supplement composition for an eye comprising on a daily dosage basis: approximately 0.5-5 mg copper, as copper glycinate, approximately 12-50 to mg zinc, as zinc glycinate, and approximately 100-500 IU natural vitamin E, lutein and coenzyme Q.

* * * * *